United States Patent [19]

Brady, deceased

[11] 3,967,490
[45] July 6, 1976

[54] VIBRATION DENSITOMETER

[75] Inventor: Edward R. Brady, deceased, late of Sierra Madre, Calif., by Barbara Jean Brady, executrix

[73] Assignee: International Telephone and Telegraph Corporation, New York, N.Y.

[22] Filed: June 27, 1975

[21] Appl. No.: 590,964

[52] U.S. Cl. .............................................. 73/32 A
[51] Int. Cl.² ........................................... G01N 9/00
[58] Field of Search .................................. 73/32 A

[56] References Cited
UNITED STATES PATENTS

| | | | |
|---|---|---|---|
| 3,444,723 | 5/1969 | Wakefield | 73/32 A |
| 3,677,067 | 7/1972 | Miller et al. | 73/32 A |
| 3,690,147 | 9/1972 | Kuenzler | 73/32 A |

Primary Examiner—James J. Gill
Attorney, Agent, or Firm—A. Donald Stolzy

[57] ABSTRACT

A vibration densitometer having a strain gage pick-up to serve at least four functions one at a time or to serve two, three or four functions in any combination of two, three or four. The strain gage is bonded to or may embody a vibrating vane or body to be immersed in a fluid. The strain gage may be bonded to a vane with glass or an epoxy or other uniting agent. If glass is used, the densitometer may undergo unusually high temperatures and still perform reliably and accurately. The strain gage may be used (1) as a pick-up in an electromechanical oscillator embodied in the densitometer, (2) as a portion of a fluid temperature indicator, (3) for instrument frequency error correction (computable in two ways) as function of temperature, and (4) for producing an indication of what the fluid density would be at a selected constant temperature.

5 Claims, 12 Drawing Figures

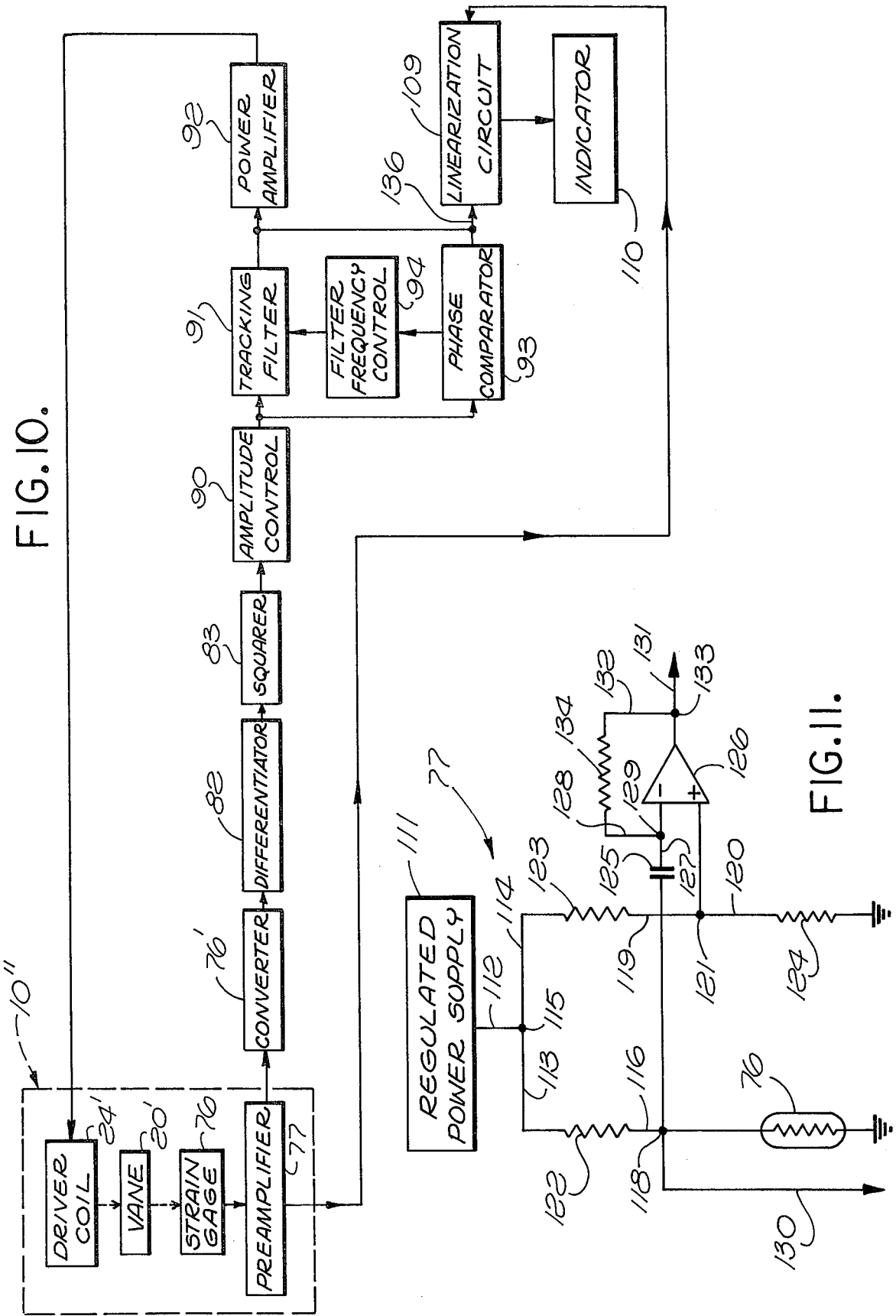

VIBRATION DENSITOMETER

BACKGROUND OF THE INVENTION

This invention relates to apparatus for producing output signals the magnitude of which are a function of the density of a fluid, and more particularly to a vibration densitometer capable of high temperature operation and/or temperature indication or computations involving temperature.

In the past, conventional pick-ups for vibration densitometers have not been adequate for use at high temperatures.

Prior art vibration densitometers further suffer frequency shifts as a function of temperature. As a result, the outputs of these instruments are inaccurate.

The volume of many fluids expand and contract with increasing and decreasing temperature, respectively. It thus would often be desirable to standardize by producing an output directly proportional to what the density of a fluid would be at a selected constant temperature. It would then be possible to determine the total mass flow or rate of mass flow in a pipeline by the use of a flowmeter producing an output which is only representative of the total volume flow or the volume rate of flow, respectively.

Prior art densitometers also fail to provide a temperature indication.

SUMMARY OF THE INVENTION

In accordance with the densitometer of the present invention, the above-described and other disadvantages of the prior art are overcome by utilizing a strain gage transducer therewith.

A feature of the invention is that the densitometer thereof may be used at high temperatures, especially when the strain gage is bonded to the densitometer vibrating vane with a sheet of glass.

Still another feature of the invention resides in the use of the self-same strain gage for a temperature sensor to correct density signal errors caused by the vibrational frequency which varies as a function of temperature.

A further feature of the invention resides in the use of equipment for correcting errors due to vibrational frequency variations in two different ways.

Still a further feature of the invention resides in the use of the strain gage as a temperature sensor to cause the densitometer to provide a density output signal directly proportional to what the density would be at a selected constant reference temperature and independent of the actual temperature, whether varying or not. Such a corrected density output signal may thus be used in total mass flowmeters, rate of mass flowmeters and otherwise.

Yet a further feature of the invention resides in the use of the strain gage as a sensor for temperature indication.

Another feature of the invention resides in the use of each feature thereof individually or in any combination.

The above-described and other advantages of the present invention will be better understood from the following detailed description when considered in connection with the accompanying drawings.

BRIEF DESCRIPTION OF THE DRAWINGS

In the drawings, which are to be regarded as merely illustrative:

FIG. 10 is a block diagram of the densitometer of the present invention;

FIG. 11 is a schematic diagram of a preamplifier shown in FIG. 10; and

DESCRIPTION OF THE PREFERRED EMBODIMENT

Figure 1:
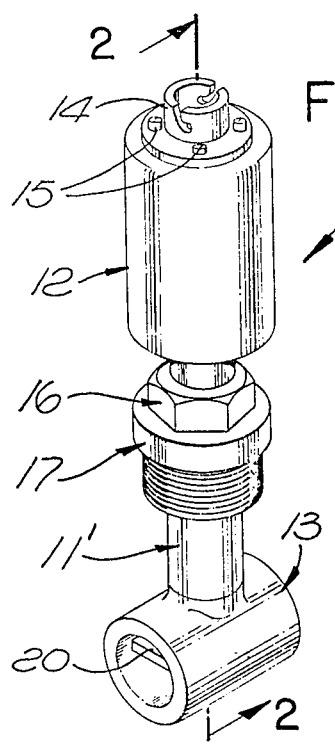
FIG. 1 is a perspective view of a densitometer probe constructed in accordance with the prior art.

In FIG. 1, the probe of the present invention is indicated at 10' having a shank 11', a housing 12' at its upper end, a tubular assembly 13 at its lower end, and a electrical connector assembly 14 at the upper end of housing 12' fixed thereto by bolts 15. Annular fittings 16 and 17 extend around shank 11' for mounting probe 10' in a hollow cylindrical extension 18 of a pipeline 19, as shown in FIG. 2.

Figure 2:
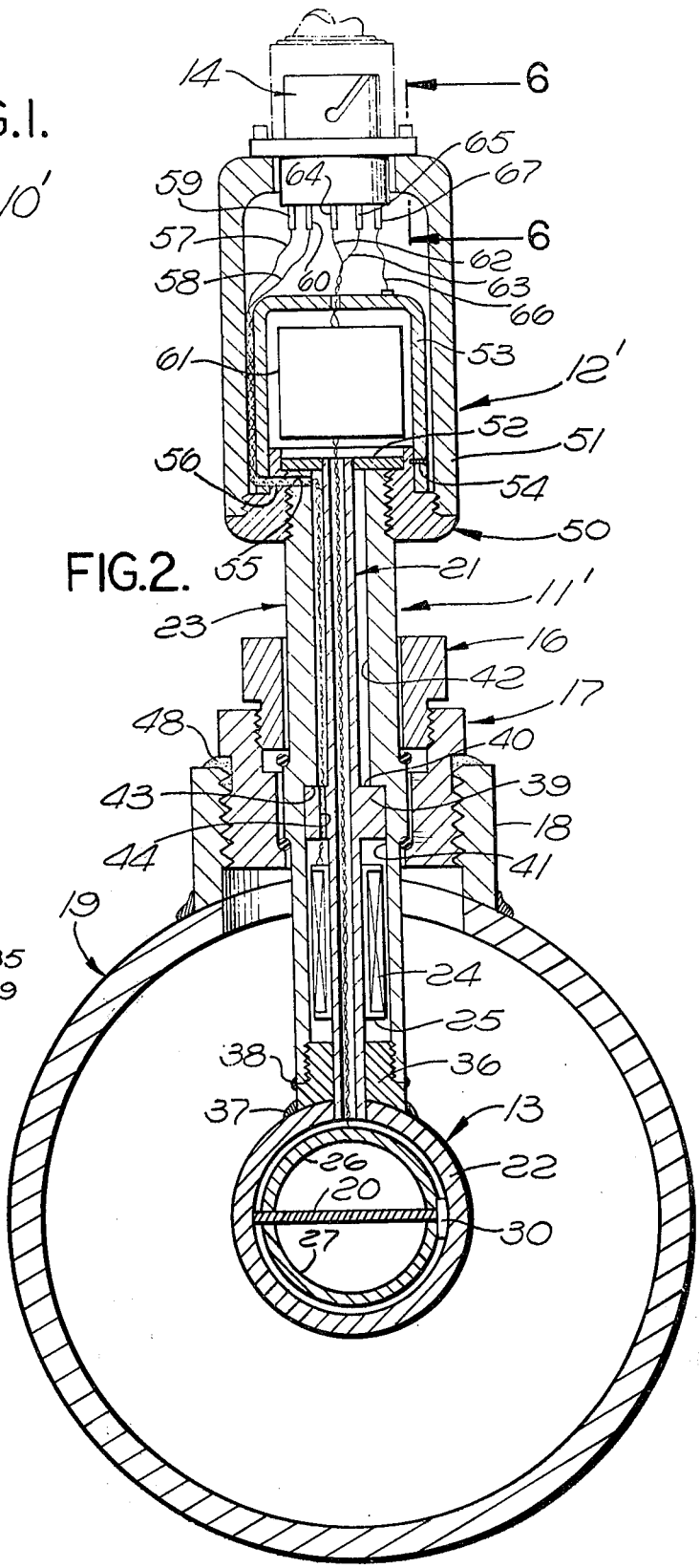
FIG. 2 is a sectional view of the probe taken on the line 2—2 shown in FIG. 1.

As shown in FIGS. 1 and 2, a stainless steel vane 20 is mounted in assembly 13 in a position perpendicular to the axis of a hollow cylindrical magnetostrictive inner tube 21. Vane 20, if desired, may be also mounted in a symmetrical position with respect to the axis of an outer sleeve 22 which houses it.

Vane 20 may be a rectangular plate having flat and parallel upper and lower surfaces as shown in FIG. 2, and may otherwise have mutually normal surfaces forming a right parallelopiped.

Shank 11' not only includes inner tube 21, but an outer magnetic tube 23. A driver coil or solenoid winding 24 wound on a nylon bobbin 25 is press fit onto the external surface of inner tube 21 and located in a space between the tubes 21 and 23 toward the lower end of shank 11'. Coil 24 is thus maintained in a substantially fixed position on inner tube 21, although the same is not necessarily critical to the operation of the device of the present invention.

Figure 3:
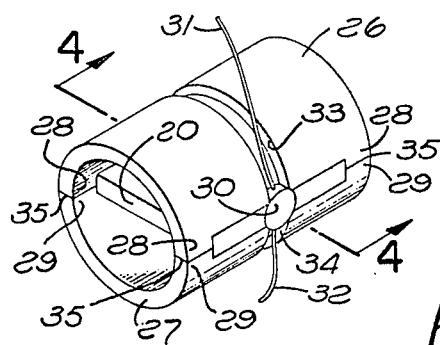
FIG. 3 is a perspective view of a group of component parts of the probe shown in FIG. 1.
Figure 4:
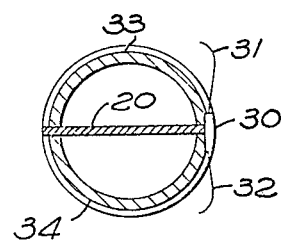
FIG. 4 is a transverse sectional view of the assembly taken on the line 4—4 shown in FIG. 3.

Vane 20 is supported between two half cylinders 26 and 27 as shown in FIGS. 2 and 3. According to the invention, the longitudinal edges of vane 20 are pressed together between half cylinders 26 and 27 with a pressure of, for example, 20,000 pounds per square inch because the assembly shown in FIG. 3 is inserted in sleeve 22 with an interference fit, sleeve 22 being heated prior to the said insertion.

Half cylinder 26 has four projections 28, and half cylinder 27 has four projections 29. Projections 28 and 29 serve to prevent longitudinal movement of vane 20 between half cylinder 26 and half cylinder 27 although the same is not likely due to the clamping pressure on vane 20 between half cylinder 26 and half cylinder 27.

Half cylinders 26 and 27, and vane 20 may be machined to have a flat or recess to receive a piezoelectric crystal 30. Crystal 30 has electrical leads 31 and 32 which extend around half cylinders 26 and 27 in grooves 33 and 34, respectively, to a point where they enter the hollow interior of inner tube 21. This entry is made at the lower end of inner tube 21, as shown in FIG. 2.

As shown in FIG. 3, projections 28 and 29 may have a slight separation at 35 to insure that the pressure contact of half cylinders 26 and 27 on vane 20 is quite high due to the said interference fit.

As shown in FIG. 2, a boss 36 is welded at 37 to sleeve 22 in a fluid tight manner. Although the device of the present invention need not always be fluid tight throughout, a glass-to-metal seal or other seal may be provided inside inner tube 21 for leads 31 and 32. Before the said interference fit is provided, if desired, crystal 30, and those portions of leads 31 and 32 in grooves 33 and 34, respectively, may be potted with an epoxy. Further, after the interference fit has been effected, the entire unit when completely assembled may be treated further by applying a bonding agent around all of the structures inside sleeve 22. Any conventional bonding process may be employed including, but not limited to, the application of a bonding agent sold under the trade name of "Locktite."

As stated previously, boss 36 may be welded to sleeve 22 at 37 in a fluid tight manner. Further, outer tube 23 may be threaded onto boss 36 and welded thereto at 38 in a fluid tight manner. For all practical purposes, boss 36 may thus be considered an integral part of outer tube 23. Boss 36, for example, is also made of a magnetic material. All of the "magnetic materials" referred to herein may be any magnetic material including, but not limited to, stainless steel. However, inner tube 21, although being magnetic, must also be magnetostrictive. Notwithstanding this limitation, it is to be noted that inner tube 21 is employed to produce vibration, and if one feature of the present invention is used without another, the use of a magnetostrictive or magnetic material may not be required, and the invention still practiced.

Inner tube 21 has an annular projection 39 with a shoulder 40. Outer tube 23 has a lower bore 41 separated from a smaller upper counter bore 42 by an annular shoulder 43. Shoulders 40 and 43 abut. From shoulder 40 to the lower end of inner tube 21, inner tube 21 is always in axial compression. That is, inner tube 21 is in compression when coil 24 is energized, but inner tube 21 is also in compression when coil 24 is deenergized. Coil 24 is energized with an undulating direct current which thus merely changes the degree of compression of inner tube 21.

Projection 39 has a hole 44 through which the electrical leads of coil 24 can pass from the location of coil 24 upwardly between tubes 21 and 23.

Figure 5:
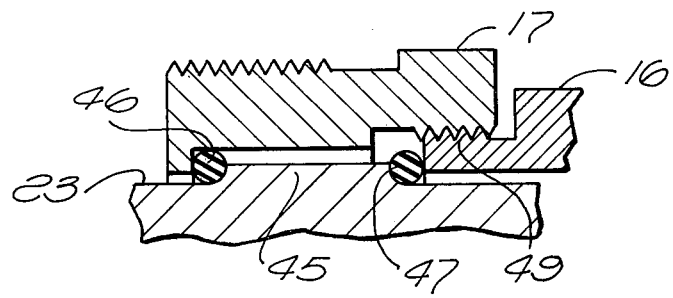
FIG. 5 is an enlarged longitudinal sectional view of a portion of the probe shown in FIG. 1.

The manner in which probe 10' is mounted in pipeline 19 is better illustrated in FIG. 5. In FIG. 5, note will be taken that outer tube 23 has an outwardly extending radial projection 45 on each side of which rubber O-rings 46 and 47 are compressed by fittings 16 and 17. Fitting 17 is threaded into extension 18 and sealed thereto by a conventional sealing compound 48 shown in FIG. 2. In FIG. 5, note will be taken that fitting 16 is threaded inside fitting 17 at 49. The amount O-rings 46 and 47 are compressed is, therefore, determined by the position of fitting 16. That is, fitting 16 is turned, for example, by a wrench, until the desired O-ring compression is reached.

From the construction illustrated in FIG. 5, note will be taken that only O-rings 46 and 47 contact outer tube 23, and that, therefore, shank 11 is never touched by either fitting 16 or fitting 17.

The construction of probe 10' is such that the leads from coil 24 are kept magnetically separate from the leads from crystal 30. This is true through a portion of housing 12' as will be described. Housing 12' has a fitting 50 threaded onto outer tube 23. A cylinder 51 is threaded to fitting 50. A washer 52 is press fit and thereby fixed in fitting 50. Inner tube 21 has an upper end which may be fixed relative to or slidable in washer 52, as desired. However, preferably the external surface of inner tube 21 at its upper end fits contiguous to or in contact with the surface of washer 52 defining the hole therethrough. A shield 53 made of a magnetic material may be fixed around fitting 50 by one or two or more screws 54. Outer tube 23 has a radial hole 55 therethrough through which the leads from coil 24 pass. Fitting 50 has a hole 56 therethrough in alignment with hole 55 through which the leads from coil 24 pass. From the outward radial extremity of hole 56, the coil leads indicated at 57 and 58 pass upwardly between cylinder 51 and shield 53 and are connected to pins 59 and 60 of the electrical connector 14. Electrical connector 14 may be a conventional five pin connector.

As stated previously, the leads 31 and 32 from crystal 30 extend upwardly through the interior of inner tube 21. At the upper end of inner tube 21, as shown in FIG. 2, leads 31 and 32 are connected to the input of a differential amplifier 61. Leads 31 and 32 thus extend outwardly through the upper opening in inner tube 21.

Differential amplifier 61 may be entirely conventional, and mounted on a conventional card, if desired. Amplifier 61 may be supported inside shield 53 by any conventional means, if desired, or simply supported by the strength of leads 31 and 32, and output leads 62 and 63 which are connected to pins 64 and 65 of connector 14, respectively. A lead 66 provides a ground connection from shield 53 to the fifth pin 67 of connector 14.

Figure 6:
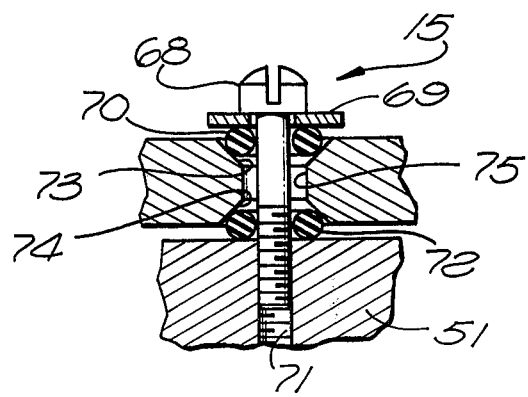
FIG. 6 is a longitudinal sectional view of a portion of mounting means for an electrical connector otherwise substantially fixed relative to the probe taken on the line 6—6 shown in FIG. 2.

The manner in which connector 14 is mounted on cylinder 51 is shown in FIG. 6. Only one bolt 15 is shown in FIG. 6 since all bolts 15 are similarly situated. In FIG. 6, bolt 15 is shown having a head 68, a washer 69 under head 68, an O-ring 70 under washer 69, and a shank 71 threaded into cylinder 51. A second O-ring 72 also extends around screw shank 71. O-ring 70 fits between the lower surface of washer 69 and a counter sunk frusto-conical hole 73 in connector 14. O-ring 72 fits between the upper surface of cylinder 51 and another counter sunk frusto-conical hole 73 in connector 14. Holes 73 and 74 are connected by a bore 75. From FIG. 6, it will be noted that all the structures shown therein may vibrate, but that the amount of vibration transmitted to connector 14 may be quite small.

One embodiment of the densitometer of the present invention is illustrated in FIG. 10. A probe 10'' is shown including a driver coil 24, a vane 20', a strain gage 76, and preamplifier 77.

Figure 7:
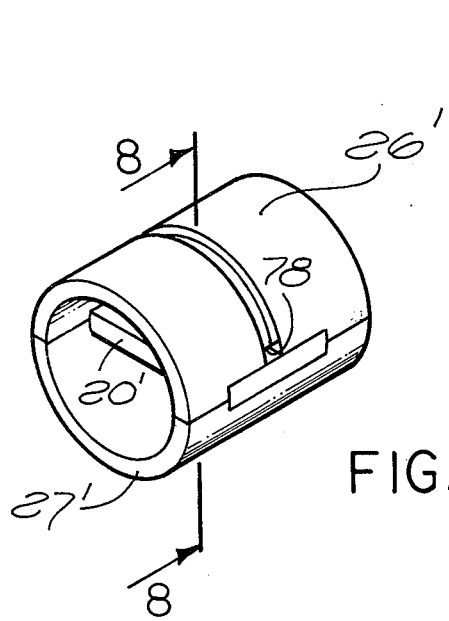
FIG. 7 is a perspective view of an assembly constructed in accordance with the present invention, which assembly is similar to but different from that shown in FIG. 3.
Figure 8:
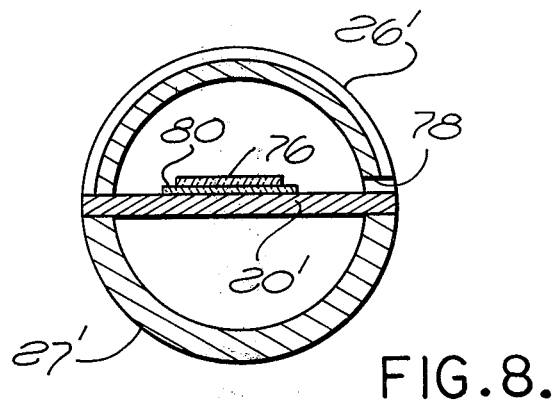
FIG. 8 is a transverse sectional view of the assembly taken on the line 8—8 shown in FIG. 7.
Figure 9:
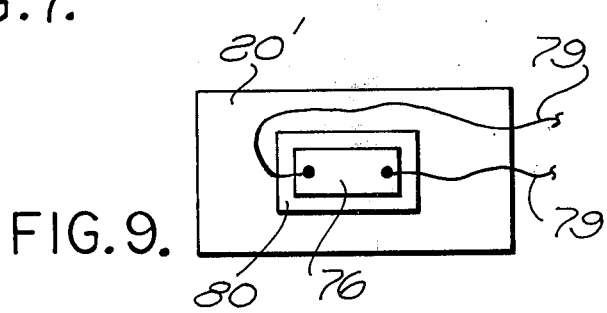
FIG. 9 is a top plan view of a vane, a strain gage and glass bonding the former two together.

Probe 10'' may be identical to probe 10' except for strain gage 76, preamplifier 77, the absence of crystal 30, and the changes shown in FIGS. 7, 8 and 9.

Comparing FIGS. 3 and 7, no provision is made for crystal 30 in FIG. 7. A notch is added in FIG. 7 as shown at 78 in FIG. 8 for the leads 79 of strain gage 76 shown in FIG. 9. Half cylinders 26' and 27' are otherwise identical to half cylinders 26 and 27 except for the elimination of groove 34 of FIG. 3 in half cylinder 27'.

Vane 20' is constructed as shown in FIGS. 7 and 8.

Strain gage leads 79 are connected to preamplifier 77 in the same way that crystal leads 31 and 32 are connected to amplifier 61, preamplifier 77 replacing amplifier 61 in FIG. 2.

Strain gage 76 is bonded to vane 20' with glass 80 in one or more conventional ways such as in the manner disclosed in U.S. Pat. No. 3,775,839.

A current-to-voltage converter 76' and a linearization circuit 109 are connected from preamplifier 77.

In FIG. 10, a differentiator 82 is connected from converter 76' to a squarer 83.

An amplitude control 90, a tracking filter 91, and a power amplifier 92 are successively connected from squarer 83 to driver coil 24'. A phase comparator 93 receives one input from the output of control 90, another input from the output of filter 91, and supplies an input to a filter frequency control 94. The output of the control 94 is employed to vary electrically the frequency location of the passband of filter 91 to where the signal having the fundamental frequency of the square wave output of control 90 to pass through filter 91 to its output with the least attenuation.

An indicator 110 is connected from linearization circuit 109.

If desired, all the structures illustrated in FIG. 10 may or may not be identical to corresponding ones illustrated in U.S. Pat. No. 3,677,067, except probe 10'' and linearization circuit 109.

Preamplifier 77 is shown in FIG. 11 including a regulated power supply 111 connected by a lead 112 to leads 113 and 114 at a junction 115. Leads 116 and 117 are connected together at a junction 118. Leads 119 and 120 are connected together at a junction 121. A resistor 122 is connected between junctions 115 and 118. A resistor 123 is connected between junctions 115 and 121. Strain gage 76 is connected between junction 118 and ground. A resistor 124 is connected from junction 121 to ground.

Strain gage 76 and resistors 122, 123 and 124 form a Wheatstone bridge. Preferably the resistance of resistor 124 is in the vicinity of the mid-range resistance of strain gage 76. The reference temperature is defined as the temperature at which $\Delta T$ is equal to zero, as explained hereinafter.

Preferably the resistance of resistor 122 is the same as that of resistor 123. The resistance of resistor 123 is preferably substantially larger than the resistance of resistor 124. A capacitor 125 is connected from junction 118 to the inverting input of a differential amplifier 126. Junction 121 is connected to the non-inverting input of differential amplifier 126.

Capacitor 125 has an electrode lead 127 which is connected to a lead 128 forming a junction at 129. Preamplifier 77 has one output lead at 130 connected from junction 118, and another output lead 131 connected from the output of amplifier 126. A lead 132 is connected to output lead 131 at junction 133. A resistor 134 is connected between junctions 129 and 133. Output lead 131 is connected to the input of converter 76' shown in FIG. 10. The output of differential amplifier 126 is connected to junction 133.

Figure 12:
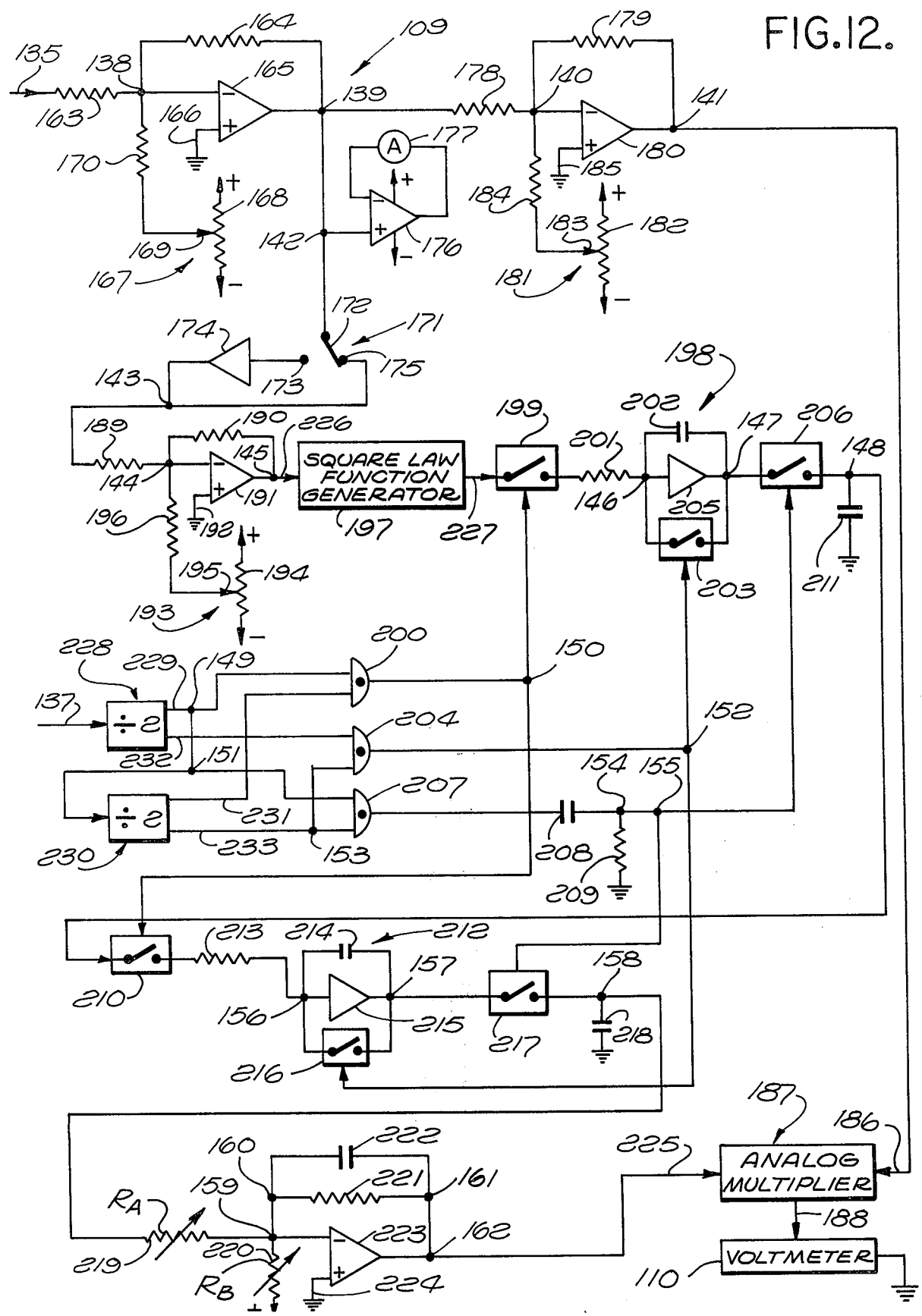
FIG. 12 is a schematic diagram of a linearization circuit shown in FIG. 10.

In FIG. 11, output lead 130 is connected to an input lead 135 in FIG. 12.

As shown in FIG. 10, phase comparator 93 has an output lead 136 connected to the input of linearization circuit 109. Linearization circuit 109 is shown in FIG. 12 having an input lead 135 thereof connected from output lead 130 of preamplifier 77 shown in FIG. 11. Linearization circuit 109 also has a second input lead 137 connected from phase comparator output lead 136 shown in FIG. 10.

In FIG. 12, indicator 110 is shown as a voltmeter calibrated in density.

In FIG. 12, junctions are indicated at 138, 139, 140, 141, 142, 143, 144, 145, 146, 147, 148, 149, 150, 151, 152, 153, 154, 155, 156, 157, 158, 159, 160, 161 and 162.

A resistor 163 is connected from input lead 135 to junction 138. A resistor 164 is connected between junctions 138 and 139, junction 138 being connected to the inverting input of a differential amplifier 165. The non-inverting input of amplifier 165 is connected to ground at 166. A potentiometer is provided at 167 having a winding 168 connected between positive and negative points of D.C. potential. Potentiometer 167 also has a wiper 169. A resistor 170 is connected from wiper 169 to junction 138.

A single pole double throw switch 171 is provided having a pole 172 connected from junction 142, a contact 173 connected to the input of an inverter 174, and a contact 175 connected to the junction 143, the output of inverter 174 also being connected to junction 143. The purpose of switch 171 is to take into account the fact that a frequency error in the vibration of vane 20' may result from a rate of change of frequency with respect to temperature which is either positive or negative.

A differential amplifier is provided at 176 having a non-inverting input connected from junction 142, and a milliammeter 177 calibrated in temperature connected from the output of amplifier 176 to the inverting input thereof. Milliammeter 177 thus reads the temperature of the fluid in which vane 20' is immersed.

A resistor 178 is connected from a junction 139 to junction 140. A resistor 179 is connected between junctions 140 and 141, junction 140 also being connected to the inverting input of a differential amplifier 180. A potentiometer 181 is provided having a winding 182 similar to winding 168. Potentiometer 181 is also provided with a wiper 183. A resistor 184 is connected from wiper 183 to junction 140. The non-inverting input of amplifier 180 is connected to ground as shown at 185. Junction 141 is connected to an input 186 of an analog multiplier 187 that has an output 188 connected to voltmeter 110.

A resistor 189 is connected between junctions 143 and 144. A resistor 190 is connected between junctions 144 and 145, junction 144 being also connected to an inverting input of a differential amplifier 191, the non-inverting input of differential amplifier 191 being connected to ground at 192. Again, a potentiometer is provided at 193 having a winding 194 similar to windings 182 and 168. Potentiometer 193 also is provided with a wiper 195. A resistor 196 is connected from wiper 195 to junction 144.

Junction 145 is connected to the input of a conventional square law function generator 197. The output of function generator 197 is impressed upon an integrator 198 through an electronic switch 199 operated by the output of an AND gate 200. Integrator 198 includes a resistor 201 connected from switch 199 to junction 146. Integrator 198 includes a capacitor 202 connected between junctions 146 and 147. Integrator 198 also includes an electronic switch 203 connected between junctions 146 and 147, and operated by the output of an AND gate 204. Integrator 198 also includes an amplifier 205 connected from junction 146 to junction 147.

The output of integrator 198 passes through an electronic switch 206 which is operated by the output of an AND gate 207 that is differentiated by a differentiator including a capacitor 208 and a resistor 209. The output of switch 206 is connected to the input of an electronic switch 210, a capacitor 211 being connected from a junction 148 connected, in turn, from the output of switch 206.

Both of the switches 199 and 210 are operated by the output of AND gate 200. The output switch 210 is impressed upon an integrator 212 which may or may not be identical to integrator 198. Thus, integrator 212 is provided with a resistor 213, a capacitor 214, an amplifier 215, and an electronic switch 216. An electronic switch 217 similar to switch 206, and operated simultaneously therewith, is connected from integrator junction 157 to a junction 158. Resistor 213 is connected from switch 210 to junction 156. Both of switches 203 and 216 are operated by the output of AND gate 204. A capacitor 218 is connected from junction 158 to ground. A variable resistor 219 is connected between junctions 158 and 159. A variable resistor 220 is connected from junction 159 to a positive D.C. source of potential. A resistor 221 is connected between junctions 160 and 161. A capacitor 222 is also connected between junctions 160 and 161. Junctions 161 and 162 are connected together. Junction 159 is connected to the inverting input of a differential amplifier 223, the non-inverting input thereof being connected to ground at 224. The output of differential amplifier 223 is connected to junction 162, and junction 162 is connected to a second input 225 of analog multiplier 187.

Function generator 197 has an input lead 226 and an output lead 227.

In FIG. 12, a divide-by-two divider 228 is connected from input lead 137 and has a 1 output lead 229 connected to a junction 149. Junctions 149 and 151 are connected together. A second divide-by-two divider 230 is provided connected from junction 151, and has a 1 output lead 231 connected to one input of AND gate 200. The AND gate 200 also has another input lead connected from junction 149.

The AND gate 204 has one input connected from the 0 output 232 of divider 228, and a second output connected from a junction 153. Junction 153 is connected from the 0 output 233 of divider 230.

One input to AND gate 207 is provided from junction 153, and the other input thereto is provided from junction 151.

OPERATION

In the operation of the densitometer of the present invention shown in FIG. 10, ambient noise will cause strain gage 76 to pick up signals in a band of frequencies including the resonant frequency of the electromagnetic oscillator that is shown in FIG. 10. The oscillator includes all structures shown in FIG. 10 except linearization circuit 109 and indicator 110. A.C. signals generated by strain gage 76 will be amplified by preamplifier 77, converted from a current to a voltage by converter 76', and differentiated by differentiator 82. The output of differentiator 82 will thus be a sine wave which is converted into a square wave by squarer 83. Amplitude control 90 may be used to reduce the output of squarer 83 to a suitable value. The frequency location of the passband of tracking filter 91 will then be varied by filter frequency control 94 to follow or pass the fundamental frequency of the output of control 90 to power amplifier 92 with a minimum attenuation.

Power amplifier 92 drives coil 24' with a signal in phase with the resonant frequency signal output of strain gage 76. The vibration of vane 20' produced by coil 24' will increase in amplitude until limted by amplitude control 90. At this time, the amplitude of the vibration will reach an approximately quiescent level. Should fluid be flowing in pipeline 19, and should the density of the fluid change, the frequency of the output signal of tracking filter 91 will also change. Linearization circuit 109 will then produce a D.C. output voltage directly proportional to density temperature corrected for both the densitometer and the fluid. The "fluid temperature correction" may or may not be considered a "correction" because it causes indicator 110 to indicate what "would be" the fluid density at a selected constant temperature even though the temperature of the fluid actually varies periodically or continuously. Indicator 110 may then be read. Indicator 110 may be a voltmeter calibrated in density, if desired.

Note will be taken that parts of the probe 10 are vibrated because the alternating signal applied to coil 24' will place varying amounts of radial compression on half cylinder 26', inner tube 21 expanding and contracting axially between shoulder 43 and the abutment of inner tube 21 at its lower end with half cylinder 26'.

The operation of the invention shown in FIG. 10, except for the character of strain gage 76 as a pick-off, preamplifier 77 and linearization circuit 109 is identical to that of the said U.S. Pat. No. 3,677,067.

Any one feature of the present invention may be used by itself or with one or more or all of the other features thereof.

Linearization circuit 109 as shown in FIG. 12, or as modified, may be employed to compute fluid density $d$ for a vane resonat frequency $f$ temperature compensated for the instrument and/or fluid expansion or contraction due to temperature changes in accordance with any one of the following equations (1), (2) and (3):

$$d = \left[\left(\frac{A}{f^2}\right)(1 + K\alpha_i \Delta T)^2 + B\right][f(x)] \quad (1)$$

where
$A$ and $B$ are calibration constants,
$K$ is one of the numbers $+1$ and $-1$, $\alpha_t$ is the temperature coefficient of the resonant period, where the resonant period is defined as the reciprocal of the resonant frequency, $\Delta T$ is the change in the temperature of the fluid from a predetermined reference temperature, $f(x)$ is one of two functions, one of said functions being a constant, the other of said functions being $f(\Delta T)$ where $$f(\Delta T) = 1 - \alpha_d \Delta T$$

and $\alpha_d$ is the temperature coefficient of the volume of said fluid;

$$d = \left[\left(\frac{A}{f^2}\right)(1 + 2K\alpha_t\Delta T) + B\right][f(x)] \quad (2)$$

$$d = \left(\left[\frac{A}{f^2}\right][f(y)] + B\right)(1 - \alpha_d\Delta T) \quad (3)$$

where $f(y)$ is one of first, second and third functions, said first function being a constant, said second and third functions being $f_a(\Delta T)$ and $f_b(\Delta T)$, respectively, where $$f_a(\Delta T) = [1 + K\alpha_t\Delta T]^2$$

and $$f_b(\Delta T) = [1 + 2K\alpha_t\Delta T].$$

If $R_a$ is the resistance of strain gage 76, and $R_b$ is the resistance of resistor 122, the potential $e_a$ of junction 118 in FIG. 11 will vary as $$e_a = (R_a E)/(R_a + R_b)$$

where $E$ is the potential of junction 115. Thus, if $$R_b >> R_a$$

$$e_a \cong (R_a E)/(R_b)$$

If $$R_a = R_o(1 + \alpha_a \Delta T)$$

where $R_o$ is the resistance of $R_a$ when $\Delta T = 0$, $\alpha_a$ is the temperature coefficient of resistance of strain gage 76, and $$\Delta T = T - T_r$$

where $T$ is temperature, and $T_r$ is reference temperature, $$e_a = (ER_o)/(R_b) \; 1 + \alpha_a \Delta T \quad (4)$$

In FIG. 12, defining $R_c$ as the resistance of resistor 163,
$R_d$ as the resistance of resistor 164,
$R_e$ as the resistance of the resistor 170,
$e_a$ as the potential of junction 139,
$E_r$ is the potential of wiper 169, it is well known that for a high gain differential amplifier 165, the potential of junction 138 is a virtual ground and the sum of the currents is effectively zero. Hence, $$\frac{e_a}{R_d} + \frac{e_o}{R_c} + \frac{E_r}{R_e} = 0$$

or $$e_a = -\frac{e_o R_c}{R_d} - \frac{E_r R_c}{R_e} \quad (5)$$

Substituting (5) in (4)

$$\Delta T = -\left[\frac{R_b}{ER_o\alpha_a}\right]\left[\frac{e_o R_c}{R_d} + \frac{E_r R_c}{R_e}\right] - \frac{1}{\alpha_a}$$

$$\Delta T = -\left[\frac{R_b R_c}{ER_o R_d \alpha_a}\right] e_o - \frac{E_r R_b R_c - ER_o R_e}{ER_o R_e \alpha_a}$$

Thus $\Delta T$ is directly proportional to $e_o$. $\Delta T$ is inverted by switch 171 if the instrument frequency error derivative with respect to temperature is negative.

The input to function generator 197 is directly proportional to $$[1 = K\alpha_t \Delta T] \quad (6)$$

Term (6) is squared and double integrated as is conventional to obtain a voltage directly proportional to $$(1/f^2)(1 + K\alpha_t \Delta T)^2$$

at junction 158. Resistors 219 and 220 supply calibration constants A and B in the conventional way. The input to analog multiplier 187 is then $$(A/f^2)(1 + K\alpha_t \Delta T)^2$$

at junction 158. Resistors 219 and 220 supply calibration constants A and B in the conventional way. The input to analog multiplier 187 is then $$(A/f^2)(1 + K\alpha_t \Delta T)^2 + B$$

Density $d$ with instrument error and fluid expansion correction is then $$d = \left[\left(\frac{A}{f^2}\right)(1 + K\alpha_t \Delta T)^2 + B\right][f(x)] \quad (7)$$

$f(x) = f(\Delta T)$ and
$f(\Delta T) = 1 - \alpha_d \Delta T$

A voltage is supplied to analog multiplier lead 186 directly proportional to $f(\Delta T)$.

Equation (7) may be simplified as in (8) below if $$K\alpha_t \Delta T_{max.} << 1$$

$$d = \left[\left(\frac{A}{f^2}\right)(1 + 2K\alpha_t \Delta T) + B\right][f(x)] \quad (8)$$

In this case function generator 197 may be omitted and leads 226 and 227 connected together.

The phrase "utilization means" as used herein and in the claims is hereby defined to mean a density indicator, a process controller or otherwise.

What is claimed is:

1. A vibration densitometer comprising: a structure mounted for immersion in a fluid; a strain gage bonded to said structure; first means connected from said strain gage to vibrate said structure at its resonant frequency $f$; second means connected from said first means for producing an output signal at said resonant frequency; and third means connected from said strain gage and said second means for producing an output directly proportional to the density $d$ of said fluid where $$d = \left[\left(\frac{A}{f^2}\right)(1 + K\alpha_t \Delta T)^2 + B\right][f(x)]$$

$A$ and $B$ are calibration constants, $K$ is one of the numbers $+1$ and $-1$, $\alpha_t$ is the temperature coefficient of the resonant period, where the resonant period is defined as the reciprocal of the resonant frequency, $\Delta T$ is the change in the temperature of said fluid from a predetermined reference temperature, $f(x)$ is one of two functions, one of said functions being a constant, the other of said functions being $f(\Delta T)$ where $F(\Delta T) = 1 - \alpha_d \Delta T$ and $\alpha_d$ is the temperature coefficient of the volume of said fluid.

2. A vibration densitometer comprising: a structure mounted for immersion in a fluid; a strain gage bonded to said structure; first means connected from said strain gage to vibrate said structure at its resonant frequency $f$; second means connected from said first means for producing an output signal at said resonant frequency; and third means connected from said strain gage and said second means for producing an output directly proportional to the density $d$ of said fluid where $$d = \left[\left(\frac{A}{f^2}\right)(1 + 2K\alpha_t \Delta T) + B\right][f(x)]$$

$A$ and $B$ are calibration constants, $K$ is one of the numbers $+1$ and $-1$, $\alpha_t$ is the temperature coefficient of resonant period, where the resonant period is defined as the reciprocal of the resonant frequency, $\Delta T$ is the change in the temperature of said fluid from a predetermined reference temperature, $f(x)$ is one of two functions, one of said functions being constant, the other of said functions being $f(\Delta T)$ where $f(\Delta T) = 1 - \alpha_d \Delta T$ and $\alpha_d$ is the temperature coefficient of the volume of said fluid.

3. A vibration densitometer comprising: a structure mounted for immersion in a fluid; a strain gage bonded to said structure; first means connected from said strain gage to vibrate said structure at its resonant frequency $f$; second means connected from said first means for producing an output signal at said resonant frequency; and third means connected from said strain gage and said second means for producing an output directly proportional to the density $d$ of said fluid where $$d = \left(\left[\frac{A}{f^2}\right][f(y)] + B\right)(1 - \alpha_d \Delta T)$$

$A$ and $B$ are calibration constants, $\alpha_d$ is the temperature coefficient of volume of said fluid, $\Delta T$ is the change in the temperature of said fluid from a predetermined reference temperature, and $f(y)$ is one of first, second and third functions, said first function being a constant, said second and third functions being $f_a(\Delta T)$ and $f_b(\Delta T)$, respectively, where $$f_a(\Delta T) = [1 + K\alpha_t \Delta T]^2$$

and $K$ is one of the numbers $+1$ and $-1$, and $\alpha_t$ is the temperature coefficient of the resonant period where the resonant period is defined as the reciprocal of the resonant frequency, and where $$f_b(\Delta T) = [1 + 2K\alpha_t \Delta T].$$

4. A vibration densitometer comprising: a structure mounted for immersion in a fluid; a strain gage bonded to said structure; first means connected from said strain gage to vibrate said structure at its resonant frequency $f$; second means connected from said first means for producing an output signal at said resonant frequency; utilization means connected from said second means; and third means connected from said strain gage for producing an output directly proportional to the temperature of said fluid.

5. The invention as defined in claim 4, wherein said utilization means includes electrical means for producing an output directly proportional to the density of the fluid.

* * * * *